(12) United States Patent
Park et al.

(10) Patent No.: US 10,050,214 B2
(45) Date of Patent: Aug. 14, 2018

(54) NEAR-ULTRAVIOLET STIMULATED LIGHT-EMITTING COMPOUND AND PRODUCTION METHOD FOR SAME

(71) Applicants: NANO CMS CO., LTD., Cheonan-si, Chungcheongnam-do (KR); KOREA RESEARCH INSTITUTE OF CHEMICAL TECHNOLOGY, Daejeon (KR)

(72) Inventors: Je Young Park, Seoul (KR); In Ja Lee, Cheonan-si (KR); Shi Surk Kim, Cheonan-si (KR); Kun Jun, Daejeon (KR); Seung Rim Shin, Daejeon (KR); Kyoung Lyong An, Daejeon (KR)

(73) Assignees: NANO CMS CO., LTD., Cheonan-si (KR); KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 15/113,379

(22) PCT Filed: Jan. 15, 2015

(86) PCT No.: PCT/KR2015/000412
§ 371 (c)(1),
(2) Date: Jul. 21, 2016

(87) PCT Pub. No.: WO2015/111872
PCT Pub. Date: Jul. 30, 2015

(65) Prior Publication Data
US 2017/0012218 A1    Jan. 12, 2017

(30) Foreign Application Priority Data
Jan. 21, 2014  (KR) ........................ 10-2014-0007221

(51) Int. Cl.
C07D 239/91    (2006.01)
H01L 51/00     (2006.01)
C09K 11/02     (2006.01)
C09K 11/06     (2006.01)
H01L 51/50     (2006.01)

(52) U.S. Cl.
CPC ........ H01L 51/0072 (2013.01); C07D 239/91 (2013.01); C09K 11/02 (2013.01); C09K 11/06 (2013.01); C09K 2211/1007 (2013.01); C09K 2211/1044 (2013.01); H01L 51/5012 (2013.01)

(58) Field of Classification Search
CPC .................................................... C07D 239/91
See application file for complete search history.

(56) References Cited

U.S. PATENT DOCUMENTS

2004/0132228 A1    7/2004  Magno et al.
2012/0288884 A1*  11/2012  Xing .................... C07D 239/91
                                              435/25

FOREIGN PATENT DOCUMENTS

KR    10-0933498    * 12/2009    ........... C07D 239/91
KR    10-2013-0129368    11/2013
KR    10-2013012936 8   * 11/2013   ........... C07D 239/91

OTHER PUBLICATIONS

PCT International Application No. PCT/KR2015/000412, International Search Report dated Mar. 23, 2015, 2 pages.

* cited by examiner

Primary Examiner — Paul V Ward
(74) Attorney, Agent, or Firm — Lee, Hong, Degerman, Kang & Waimey

(57) ABSTRACT

The present invention relates to a near-ultraviolet stimulated light-emitting compound, and more specifically relates to a fluorescent quinazolinone compound which is stimulated in the near ultraviolet region. The fluorescent quinazolinone compound according to the present invention is colorless in daylight but exhibits a high fluorescent intensity when irradiated with light in the near ultraviolet region. Also, the fluorescent quinazolinone compound can be easily used with printed and plastic molded products since the compound not only has a high degree of light fastness and thermal stability but also high dispersibility.

14 Claims, No Drawings

NEAR-ULTRAVIOLET STIMULATED LIGHT-EMITTING COMPOUND AND PRODUCTION METHOD FOR SAME

CROSS-REFERENCE TO RELATED APPLICATIONS

This application is the National Stage filing under 35 U.S.C. 371 of International Application No. PCT/KR2015/000412, filed on Jan. 15, 2015, which claims the benefit of earlier filing date and right of priority to Korean Patent Application No. 10-2014-0007221, filed on Jan. 21, 2014, the contents of which are all hereby incorporated by reference herein in their entirety.

TECHNICAL FIELD

The present disclosure relates to a near-ultraviolet stimulated light-emitting compound, and more particularly, to a fluorescent quinazolinone compound stimulated in the near-ultraviolet region and a method for producing the same.

DISCUSSION OF THE RELATED ART

Generally, a compound stimulated in near-ultraviolet region is stimulated by ultraviolet rays in a range of 365 nm wavelength to emit intense visible light wavelength. The compound stimulated in the near-ultraviolet region and emitting visible light wavelength is colorless in the daylight region, but exhibits different fluorescence and durability depending on positions and types of the substituent bound to ligand, when stimulated by ultraviolet rays.

The near-ultraviolet stimulated compound may be widely used in the industrial application field that utilizes light emitting feature. Most representatively, the near-ultraviolet stimulated compound may be applied to image display devices, organic light emitting diodes, electro-optical devices and analytic means, and may be used in security marking.

As the compound discharged through excitation by ultraviolet rays has the higher fluorescent intensity, fastness, thermal stability, and dispersibility, the higher fluorescent feature may be exhibited in coating and plastic molding.

Therefore, research on positions and types of substituents is the most important, in order to design a near-ultraviolet stimulated light-emitting compound having excellent feature such as high fluorescent intensity, as well as high fastness, thermal stability, and dispersibility.

SUMMARY

Therefore, an object of the present disclosure is to provide a fluorescent quinazolinone compound having high degree of light fastness and thermal stability and stimulated in near-ultraviolet region.

In addition, another object of the present disclosure is to provide a near-ultraviolet stimulated light-emitting compound including the quinazolinone compound and a binder.

Still another object of the present disclosure is to provide a producing method of the quinazolinone compound.

In order to achieve at least the above objects, in whole or in part, and in accordance with the purposes of the present disclosure, as embodied and broadly described, and in a general aspect, there is provided a near-ultraviolet stimulated light-emitting compound, represented by a following chemical formula I:

[Chemical Formula I]

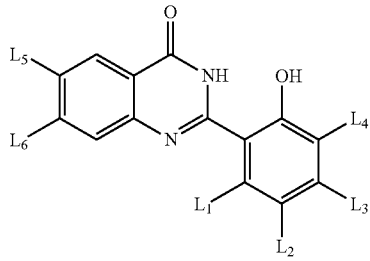

wherein in the chemical formula I, the $L_1$, $L_2$, $L_3$ and $L_4$ may be respectively and optionally substituted by substituents each independently selected from hydrogen, halogen, hydroxy, cyanide, $C_1$-$C_8$ alkoxy, $C_1$-$C_8$ alkyl, $C_5$-$C_6$ aryl and $C_1$-$C_8$ alkylamino; and the $L_5$ and $L_6$ may be respectively and optionally substituted by substituents each independently selected from hydrogen and halogen.

In some exemplary embodiments, the halogen may be fluorine (F) or chlorine

In some exemplary embodiments, the $L_1$ and $L_4$ may be hydrogen.

In some exemplary embodiments, the $L_1$ may be hydrogen, and the $L_2$ may be chlorine (Cl).

In some exemplary embodiments, the $L_1$ may be hydrogen, and the $L_2$ may be fluorine (F).

In some exemplary embodiments, the compound may be 7-chloro-2(5-chloro-2-hydroxyphenyl)quinazoline-4(3H)-on; or 6-chloro-2(5-chloro-2-hydroxyphenyl)quinazoline-4(3H)-on.

In some exemplary embodiments, the compound may be selected from a group consisting of:
7-chloro-2(4-chloro-2-hydroxyphenyl)quinazoline-4(3H)-on;
2-(5-fluoro-2-hyroxyphenyl)quinazoline-4(3H)-on;
2-(3-choloro-2-hydroxyphenyl)quinazoline-4(3H)-on;
2-(2-chloro-6-hyrdoxyphenyl)quinazoline-4(3H)-on;
6-chloro-2-(4-chloro-2-hydroxyphenyl)quinazoline-4(3H)-on; and
2-(4-chloro-2-hyroxyphenyl)quinazoline-4(3H)-on.

In some exemplary embodiments, the near-ultraviolet stimulated light-emitting compound may further comprise: at least one binder selected from a group consisting of acrylic polymer, polyamide, polyester, polyethylene terephthalate, polycarbonate and polypropylene.

In another general aspect, there is provided a method for producing the near-ultraviolet stimulated light-emitting compound, the method comprising: condensation-reacting a 2-aminobenzamide optionally substituted by a substituent independently selected from hygrogen and halogen; and a phenylaldehyde optionally substituted by a substituent independently selected from hydrogen, halogen, hydroxy, cyanide, C1-C8 alkoxy, C1-C8 alkyl, C5-C6 aryl and C1-C8 alkylamino.

In some exemplary embodiments, the condensation reaction may be accelerated by a catalyst.

In some exemplary embodiments, the catalyst may be at least one selected from a group consisting of potassium permanganate, dichloro cyano benzoquinone, sodium bisulfite, scandium triflate, ammonium chloride, cupric chloride, stannic chloride, trifluoroacetic acid, tetrabutylammonium bromide and p-toluenesulfonic acid.

In some exemplary embodiments, the condensation reaction is performed in at least one solvent selected from a group consisting of acetonitrile, ethyl alcohol, dimethylacetamide and dimethylformamide.

Advantage

The fluorescent quinazolinone compound according to an exemplary embodiment of the present disclosue is colourless in daylight but may exhibit a high fluorescent intensity when irradiated with light in the near ultraviolet region. In addition, the fluorescent quinazolinone compound can be easily used with printed and plastic molded products since the compound not only has a high degree of light fastness and thermal stability but also high dispersibility.

DETAILED DESCRIPTION

The following description is not intended to limit the present disclosure to the form disclosed herein. Consequently, variations and modifications commensurate with the following teachings, and skill and knowledge of the relevant art are within the scope of the present disclosure. The embodiments described herein are further intended to explain modes known of practicing the present disclosure and to enable others skilled in the art to utilize the present disclosure in such, or other embodiments and with various modifications required by the particular application(s) or use(s) of the present disclosure. When it is determined that a detailed description about known function or structure relating to the present disclosure may evade the main point of the present disclosure, the detailed description may be omitted.

The terms including ordinal numbers such as "first" or "second" may be used for description of various elements. However, the elements shall not be limited by such the terms. The terms are used merely to distinguish a particular element from another element.

It will be understood that when an element is referred to as being "connected" or "coupled" to another element, it can be directly connected or coupled to the other elements or intervening elements may be present. In contrast, when an element is referred to as being "directly connected" or "directly coupled" to another element, there are no intervening elements present.

The terminology used herein is for the purpose of describing particular embodiments only and is not intended to be limiting of the general inventive concept. As used herein, the singular forms "a", "an" and "the" are intended to include the plural forms as well, unless the context clearly indicates otherwise. The terms mentioned herein are used merely for description of a particular exemplary embodiment. Thus, they are not intended to limit the scope of the present disclosure. The singular expression includes numeral expression thereof unless it has a clearly different meaning in the context. In the present disclosure, the terms such as "include" or "have" are state that there may be in existence of features, numbers, steps, functions, elements, components described herein, or compositions thereof. Therefore, they shall not be understood as to exclude the possibility of existence or addition of one or more other features, numbers, steps, functions, elements, components described herein, or compositions thereof.

Definitions

As used herein, the term "daylight" refers to all outdoor rays such as the light of the sun or the skylight.

As used herein, the term "excited excitation (or stimulation)" refers to a state where an atom or a molecule absorbs energy by light or heat from external source such that the energy level of orbital electrons has ascended.

As used herein, the term "alkyl" refers to radicals of saturated aliphatic groups including straight-chain alkyl groups, branched-chain alkyl groups, cycloalkyl (alicyclic) groups, cycloalkyl groups substituted by alkyls, and alkyl groups substituted by cycloalkyls. The term "alkyl" may further include oxygen, nitrogen, sulfur, or phosphorus atoms, where the oxygen, nitrogen, sulfur, or phosphorus atoms substitute at least one carbon of a hydrocarbon backbone.

In some exemplary embodiments, the straight-chain alkyl or the branched-chain alkyl may have, in its backbone, carbon atoms in a number of no more than twenty (e.g. a $C_1$-$C_{20}$ for straight chain, $C_3$-$C_{20}$ for branched chain), preferably no more than fifteen, more preferably no more than eight. In the same manner, preferred cycloalkyls may have, in their ring structure, carbon atoms in a number of 3-10, preferably in a number of 3, 4, 5, 6, or 7.

In addition, the term "alkyl" is intended to include both of "unsubstituted alkyls" and "substituted alkyls", the latter of which refers to alkyl moieties having substituents substituting a hydrogen on at least one carbon of a hydrocarbon backbone. The substituents may include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, acoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

It may be understood by those skilled in the art that a substituted moiety on the hydrocarbon chain may be spontaneously substituted in a suitable case. Cycloalkyl may be further substituted with, for example, the above-mentioned substituent. An "alkylaryl" moiety is an alkyl substituted with an aryl (for example, phenylmethyl(benzyl). In addition, the term "alkyl" includes unsaturated aliphatic group capable of being substituted with the above-mentioned alkyl and having a similar length and may include at least one double or triple bond, respectively.

Unless the number of carbon atoms is described otherwise, a "lower alkyl" group may refer to the above-defined alkyl group having 1 to 10, preferably 1 to 6, and more preferably 1 to 4 carbon atoms in its backbone structure that may be a straight chain or a branched chain. An example of the lower alkyl group includes methyl, ethyl, n-propyl, propyl, tert-butyl, hexyl, heptyl, octyl, and the like. In some exemplary embodiments, the term "lower alkyl" includes a straight-chain alkyl having 4 or less carbon atoms in the backbone thereof. For example, the lower alkyl may include $C_1$-$C_4$ alkyl.

As used herein, the term "associated with" refers to a condition at which a chemical substance, a compound or a moiety thereof and a binding pocket or binding site of protein are closely positioned. The bond may be a non-covalent or covalent bond (energetically preferred by a hydrogen bond or Van der Waals or electrostatic interaction).

As used herein, the term "halogen" refers to —F, —Cl, —Br, or —I.

As used herein, the term "hydroxyl" refers to —OH.

As used herein, the term "hetero atom" refers to an atom of any element except for carbon or hydrogen. Some examples of the hetero atoms may be nitrogen, oxygen, sulfur, and phosphorus.

As used herein, the term "optionally substituted" is intended to include an unsubstituted group or a group substituted by at least one suitable group except for hydrogen at one or more possible positions (that may be equal to or different from each other), generally, 1, 2, 3, 4, or 5 positions.

An example of the selective substituent may include carbocyclic and heterocyclic groups, as well as hydroxyl, halogen, cyano, nitro, $C_1$-$C_8$ alkyl, $C_2$-$C_8$ alkenyl, $C_2$-$C_8$ alkynyl, $C_1$-$C_8$ alkoxy, $C_2$-$C_8$ alkylether, $C_3$-$C_8$ alkanone, $C_1$-$C_8$ alkylthio, amino, mono- or di-($C_1$-$C_8$ alkyl)amino, halo $C_1$-$C_8$ alkyl, halo $C_1$-$C_8$ alkoxy, $C_1$-$C_8$ alkanoyl, $C_2$-$C_8$ alkanoyloxy, $C_1$-$C_8$ alkoxycarbonyl, —COOH, —CONH$_2$, mono- or di-($C_1$-$C_8$ alkyl)aminocarbonyl, —SO$_2$NH$_2$ and/or mono- or di-($C_1$-$C_8$ alkyl)sulfonamide.

In addition, the optional substitution may be described by a phase "substituted by 0 to X substituents", wherein X is the maximum number of possible substituent. An optionally substituted group may be substituted by 0 to 2, 3 or 4 independently selected substituents (that is, the group may not be substituted, or the group may be substituted by a number below the maximum number of substituents enumerated).

As used herein, the term "chiral" refers to molecules which have the property of non-superimposability of the mirror image partner, while the term "achiral" refers to molecules which are superimposable on their mirror image partner.

As used herein, the term "diastereomer" refers to a stereoisomer with two or more centers of chirality and whose molecules are not mirror images of one another.

As used herein, the term "isomer" or "stereoisomer" refers to compounds which have identical chemical constitution, but differ with regard to the arrangement of the atoms or groups in space.

The term "enantiomers (mirror image isomers)" refers to two stereoisomers of a compound which are non-superimposable mirror images of one another. An equimolar mixture of two enantiomeric species may be referred to as "racemic mixture" or "racemate". A compound of the present disclosure may include one or more centers of chirality, and therefore, may be present as a racemate or a racemic mixture, a single enantiomer, an individual diastereomer, and a mixture of diastereomers. All isomeric forms of the compound are definitely included in the present disclosure. For example, the compound of the present disclosure may be represented as a plurality of tautomeric forms, and the present disclosure definitely includes all tautomeric forms of the compound described in the present disclosure. All isomeric forms of the compound are definitely included in the present disclosure. All crystalline forms of the compound described in the present disclosure are definitely included in the present disclosure.

Herein, a description for a list of chemical functional groups within any of various definitions includes various definitions of any single functional group or combination of functional groups described. Herein, descriptions for various exemplary embodiments include a single exemplary embodiment, any other exemplary embodiment, or an exemplary embodiment as a combination of parts thereof. Herein, descriptions for various exemplary embodiments include a single exemplary embodiment, any other exemplary embodiment, or an exemplary embodiment as a combination of parts thereof.

Compound of the Present Disclosure

According to an aspect of the present disclosure, there may be provided a near-ultraviolet stimulated light-emitting compound represented by chemical formula I.

[Chemical Formula I]

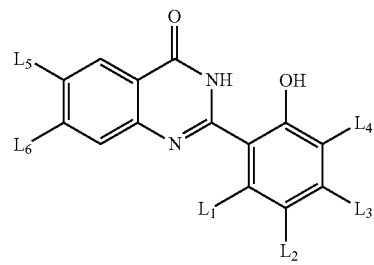

Here, the $L_1$, $L_1$, $L_3$ and $L_4$ may be respectively and optionally substituted by substituents each independently selected from hydrogen, halogen, hydroxy, cyanide, $C_1$-$C_8$ alkoxy, $C_1$-$C_8$ alkyl, $C_5$-$C_6$ aryl and $C_1$-$C_8$ alkylamino; and the $L_5$ and $L_6$ may be respectively and optionally substituted by substituents each independently selected from hydrogen and halogen.

According to an exemplary embodiment, the halogen may be fluorine (F) or chlorine (Cl).

According to an exemplary embodiment, the $L_1$ and $L_4$ may be hydrogen.

According to an exemplary embodiment, the $L_1$ may be hydrogen, and the $L_2$ may be chlorine (Cl).

According to an exemplary embodiment, the $L_1$ may be hydrogen, and the $L_2$ may be fluorine (F).

Exemplary constitutions of the compound of the present disclosure are illustrated in the following.

Unless otherwise specified herein, stereochemistry of chiral carbons may be present independently in in (RS) form, R form or S form. The constitution of the compound descried in the present disclosure may include particular —NH—, —NH$_2$ (amino) and —OH (hydroxyl) groups in positions corresponding to those of hydrogen atom(s) which are not clearly shown.

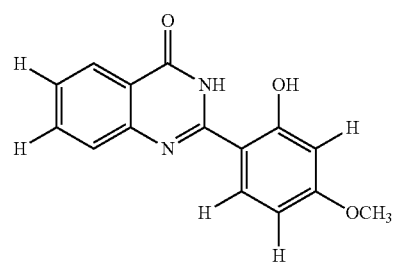 [SMILES: COc1ccc(-c2nc3ccccc3c(=O)[nH]2)c(O)c1]

2-(2-hydroxy-4-methoxyphenyl)quinazoline-4-(3H)-on;

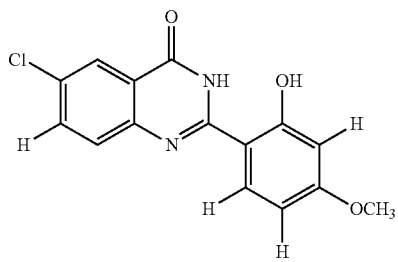 [SMILES: COc1ccc(-c2nc3ccc(Cl)cc3c(=O)[nH]2)c(O)c1]
6-chloro-2-(2-hydroxy-4-methoxyphenyl)quinazoline-4(3H)-on;
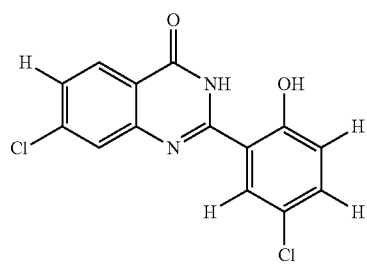
7-chloro-2-(5-chloro-2-hydroxyphenyl)quinazoline-4(3H)-on;
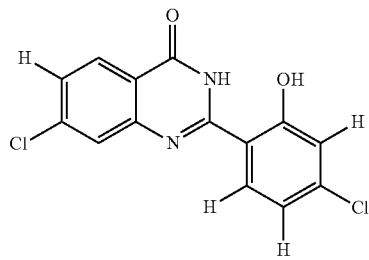 [SMILES: O=c1[nH]c(-c2ccc(Cl)cc2O)nc2cc(Cl)ccc12]
7-chloro-2-(4-chloro-2-hydroxyphenyl)quinazoline-4(3H)-on;
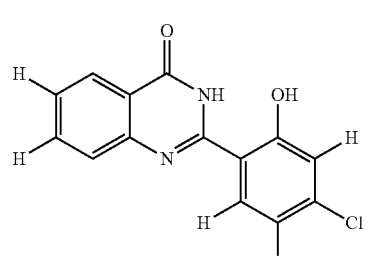
2-(4-chloro-2-hydroxyphenyl)quinazoline-4(3H)-on;
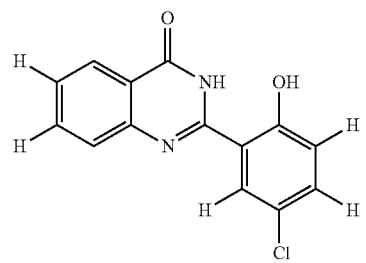
2-(5-chloro-2-hydroxyphenyl)quinazoline-4(3H)-on;
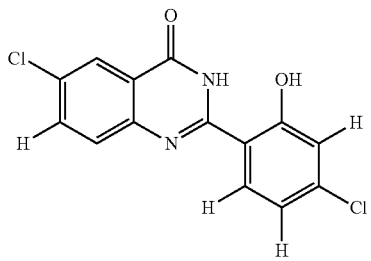 [SMILES: O=c1[nH]c(-c2ccc(Cl)cc2O)nc2ccc(Cl)cc12]
6-chloro-2-(4-chloro-2-hydroxyphenyl)quinazoline-4(3H)-on;
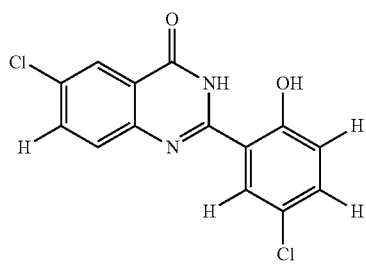
6-choloro-2-(5-chloro-2-hydroxyphenyl)quinazoline-4(3H)-on;
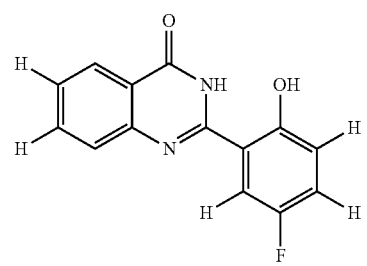 [SMILES: O=c1[nH]c(-c2cc(F)ccc2O)nc2ccccc12]
2-(5-fluoro-2-hyroxyphenyl)quinazoline-4(3H)-on;

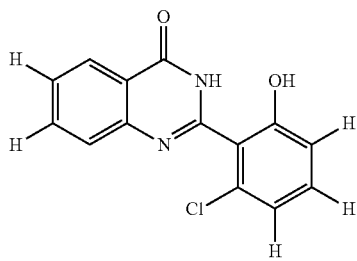 [SMILES: O=c1[nH]c(-c2c(O)cccc2Cl)nc2ccccc12]

2-(2-chloro-6-hyrdoxyphenyl)quinazoline-4(3H)-on;

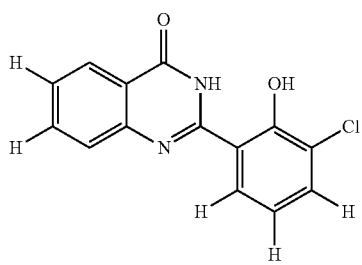 [SMILES: O=c1[nH]c(-c2cccc(Cl)c2O)nc2ccccc12]

2-(3-choloro-2-hydroxyphenyl)quinazoline-4(3H)-on.

Composition of the Present Disclosure

According to another aspect of the present disclosure, there may be provided a near-ultraviolet stimulated light-emitting composition, comprising: the near-ultraviolet stimulated light-emitting compound; and at least one binder selected from a group consisting of acrylic polymer, polyamide, polyurethane, polyester, polyethylene terephthalate, polycarbonate and polypropylene.

According to an exemplary embodiment, the near-ultraviolet stimulated light-emitting composition of the present disclosure may be used, not only in security printouts, plastic cards used as data carriers (e.g. check cards, credit cards, certification cards, etc.), but also in the laminating process of bank notes, certificates, and passports.

Method for Producing the Compound and Composition of the Present Disclosure

According to still another aspect of the present disclosure, there may be provided a method for producing the near-ultraviolet stimulated light-emitting compound of any one of claims 1 to 6, the method comprising: condensation-reacting a 2-aminobenzamide optionally substituted by a substituent independently selected from hygrogen and halogen; and a phenylaldehyde optionally substituted by a substituent independently selected from hydrogen, halogen, hydroxy, cyanide, C1-C8 alkoxy, C1-C8 alkyl, C5-C6 aryl and C1-C8 alkylamino.

A schematic reaction formula of the condensation reaction may be represented by chemical formula II as follows.

[Chemical Formula II]

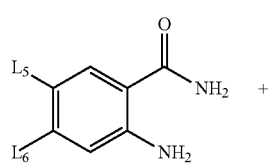

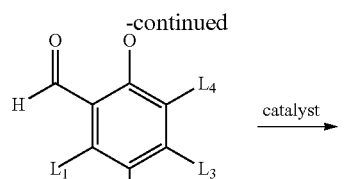

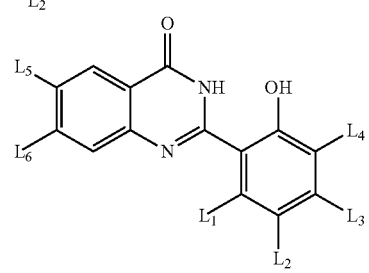

According to an exemplary embodiment of the present disclosure, the condensation reaction may be accelerated by a catalyst. The fluorescent intensity discharged from the compound when irradiated with near-ultraviolet rays may be different depending on the catalyst used in the condensation reaction.

According to an exemplary embodiment of the present disclosure, the catalyst may be a metallic salt catalyst. For example, the catalyst may be at least one selected from a group consisting of potassium permanganate, dichloro cyano benzoquinone, sodium bisulfite, scandium triflate, ammonium chloride, cupric chloride, stannic chloride, trifluoroacetic acid, tetrabutylammonium bromide and p-toluenesulfonic acid. However, the present disclosure is not limited to the examples listed in the above.

According to an exemplary embodiment, the condensation reaction may be performed in at least one solvent selected from a group consisting of acetonitrile, ethyl alcohol, dimethylacetamide and dimethylformamide.

Unless otherwise specified herein, the compound and composition of the present disclosure may be produced by a means known in the field of organic synthesis, except for the producing method described in the above. The method for optimizing reaction conditions required to minimize competitive by-products is well known in the art to which the present disclosure pertains. A high-speed parallel synthesis equipment and a computer-controlled microreactor may be appropriately used in optimizing reaction and scaling up (for example, as described in Design And Optimization in Organic Synthesis, $2^{nd}$ Edition, Carlson R, Ed, 2005; Elsevier Science Ltd.; Jahnisch, K et al, Angew. Chem. Int. Ed. Engl. 2004 43:406; and documents references herein). Those skilled in the art may determine additional reaction procedures and protocols using commonly used structure-search database software, e.g. SciFinder® (CAS division of the American Chemical Society) and CrossFire Beilstein® (Elsevier MDL), etc.

As understandable by those who skilled in the art, it will be apparent that the method for compounding the composition including formulas and embodiments of the present application falls within the scope of ordinary skill in the art. In addition, various compounding steps may be performed in alternative order or sequence in order to obtain preferable compound. Furthermore, the conditions such as solvent, temperature and reaction duration are discussed herein merely for the illustrated purposes, and one skilled in the art will appreciate that changing in these reaction conditions may cause production of preferred compound of the present disclosure.

Hereinafter, the present disclosure will be described in more detail through exemplary embodiments. However, these embodiments are merely examples and do not limit the scope of the present disclosure. It will be apparent that the persons who skilled in the art of the present disclosure may perform various transformed or modified embodiments within the limit of the claimed technical spirit of the present disclosure.

Method for Producing Near-Ultraviolet Stimulated Light-Emitting Quinazolinone Compound In order to ascertain the characteristic of quinazolinone compound including positions and types of different substituents, optionally substituted quinazolinone compounds were produced according to the following method:

Optionally substituted phenylaldehyde 5.97g and optionally substituted 2-aminobenzamide 7.98 g were added to ethyl alcohol 540 Ml in an 1 L four-neck round-bottom flask, and then the mixture was stirred until a transparent solution was obtained. After the phenyl aldehyde and the 2-aminobenzamide were all dissolved, a solution of ethyl alcohol 72 Ml added with cupric chloride 15.8 g was added dropwise with stirring to the above solution for a predetermined period of time. As the cupric chloride, which is a catalyst, was added dropwise, an optionally substituted quinazolinone compound was generated as a precipitate. Then, the optionally substituted quinazolinone compound was separated and dried.

The optionally substituted quinazolinone compounds produced according to the above method had in common the constitution represented by chemical formula I. $L_1$~$L_6$ substituents for compositions in respective embodiments are illustrated in the following TABLE 1.

TABLE 1

| Embodiment No. | $L_1$ | $L_2$ | $L_3$ | $L_4$ | $L_5$ | $L_6$ |
|---|---|---|---|---|---|---|
| 1 | —H | —H | —H | —H | —H | —H |
| 2 | —H | —H | —H | —H | —Cl | —H |
| 3 | —H | —H | —H | —H | —H | —Cl |
| 4 | —H | —Cl | —H | —H | —H | —H |
| 5 | —H | —Cl | —H | —H | —Cl | —H |
| 6 | —H | —Cl | —H | —H | —H | —Cl |
| 7 | —H | —H | —OCH$_3$ | —H | —H | —H |
| 8 | —H | —H | —OCH$_3$ | —H | —Cl | —H |
| 9 | —H | —H | —OCH$_3$ | —H | —H | —Cl |
| 10 | —H | —H | —Cl | —H | —H | —H |
| 11 | —H | —H | —Cl | —H | —Cl | —H |
| 12 | —H | —H | —Cl | —H | —H | —Cl |
| 13 | —H | —F | —H | —H | —H | —H |
| 14 | —H | —F | —H | —H | —Cl | —H |
| 15 | —H | —F | —H | —H | —H | —Cl |
| 16 | —Cl | —H | —H | —H | —H | —H |
| 17 | —H | —H | —H | —Cl | —H | —H |

Result of Measuring Fluorescent Intensity

The obtained quinazolinone compound was irradiated with near-UV light in the wavelength of 365 nm, and the intensity of discharged fluorescence was measured. The fluorescent intensity was measured using a fluorescence spectrometer (DARSA-5000, PSI Co., Ltd.), under the condition of 365 nm stimulation wavelength, cumulative average of five-time measurements, and 1024×128 CCD sensor shape. In addition, measurement of residual fluorescent intensity after artificial light exposure was repeated identically according to ASTM G 154-06 Cycle 1 standard.

The results of fluorescence intensity measurements are shown in TABLE 2 below.

TABLE 2

| Embodiment No. | Fluorescent Intensity (UV light 365 nm stimulated) Solid Phase | Fluorescent Color Solid Phase | The remaining fluorescence intensity (after artificial light exposure) Coating (10%) |
|---|---|---|---|
| 1 | +++++ | Green | 25% |
| 2 | +++++ | Green | 30% |
| 3 | − | Non-fluorescent | — |
| 4 | ++++ | Green | 65% |
| 5 | ++ | Yellow | 80% |
| 6 | +++ | Yellow-green | 70% |
| 7 | ++ | Turquoise | 40% |
| 8 | ++ | Turquoise | 45% |
| 9 | − | Non-fluorescent | — |
| 10 | ++++ | Turquoise | 60% |
| 11 | ++++ | Turquoise | 70% |
| 12 | +++ | Turquoise | 40% |
| 13 | +++++ | Green | 65% |
| 14 | − | Non-fluorescent | — |
| 15 | − | Non-fluorescent | — |
| 16 | ++++ | Green | 60% |
| 17 | ++++ | Green | 60% |

−: not measured;
+: very low;
++: low;
+++: medium;
++++: high;
+++++: very high According to the results shown in TABLE 2, in embodiments 4-8, 10-13, 16 and 17, the compounds exhibited a remaining fluorescence intensity of above 40%. All compounds except for those in embodiments 3, 9, 14 and 15 were excited by the near-ultraviolet irradiation to exhibit the fluorescence emission.

Compounds of Embodiments 6 and 11

As shown in TABLE 3 below, 365 nm wavelength of near-ultraviolet light was irradiated to the compounds of embodiments 6 and 11, to measure the intensity of fluorescence discharged up to the range of 400~700 nm. Further, the melting point was measured using the melting point measuring instrument (M5000, KRÜSS GmbH), by assuming that the phase change is at the point where the change in transmissivity reaches 20%. Solubility in organic solvents was measured with respect to eight product items.

TABLE 3

| Items | Embodiment 6 | Embodiment 11 |
|---|---|---|
| Fluorescence Intensity | +++ | ++++ |
| Em$_{max}$ (nm) | 527 | 490 |
| Melting Point (° C.) | >390 | 370 |
| Solubility | | |
| Acetone | <0.1 | <0.1 |
| Ethyl Alcohol | − | − |
| Water | <0.1 | <0.1 |
| Normal Hexane | − | − |
| 5% Hydrochloric Acid Solution | − | − |
| 2% Sodium Hydroxide (Caustic Soda) Solution | Resolved | Resolved |

TABLE 3-continued

| Items | Embodiment 6 | Embodiment 11 |
| --- | --- | --- |
| Ethyl Acetate | – | – |
| Toluene | <0.1 | <0.1 |

–: not measured;
+: very low;
++: low;
+++: medium;
++++: high;
+++++: very high As described in TABLE 3 in the above, it can be ascertained that the compounds of embodiments 6 and 11 have high fluorescent intensity, high thermal stability, and low solubility in organic solvents as well.

Application Examples

In addition, compositions respectively containing 10% compounds of embodiments 6 and 11 were sealed on a non-florescent paper, using a grinder and an offset plate printing press (HFT-225, HONGFAT machinery manufacturing Co., Ltd.). Chemical resistance tests and solvent resistance tests were performed on the printed material for 30 minutes at 23° C. with respect to each of nine product items. Furthermore, grades with reference to the standard and remaining fluorescence intensities were measured by irradiating the near-ultraviolet light of 365 nm wavelength, using a weatherability tester (QUV, Q-LAB Corporation), according to ASTM G154-06 Cycle No. 1 standard (except for the condensation conditions). The measurement results are shown in TABLE 4 below.

TABLE 4

| Items | Application Example 1 Film, 10% Remaining Fluorescence Intensity (comparing to the initial state) | Application Example 2 Film, 10% Remaining Fluorescence Intensity (comparing to the initial state) |
| --- | --- | --- |
| Initial State | +++++ | +++++ |
| Acid Solution | +++++ | +++++ |
| Alkaline Solution | +++++ | +++++ |
| Artificial Sweat Solution | +++++ | +++++ |
| Ethyl Acetate | +++ | +++ |
| Ethyl Alcohol | +++++ | +++++ |
| Petroleum Solvents | +++++ | +++++ |
| Acetone | ++ | ++ |
| 5% Soap Solution (80° C.) | – | – |
| Hot Water (100° C.) | +++++ | +++++ |
| Light Fastness Grade | 4 | =4 |
| Remaining Fluorescence Intensity (comparing to the initial state) | 70% | 70% |

–: not measured;
+: very low;
++: low;
+++: medium;
++++: high;
+++++: very high As described in TABLE 4 in the above, the compounds of embodiments 6 and 11 exhibited relatively high remaining fluorescence intensity in almost all solvents except for the 5% soap solution, to have high solvent resistance. Also in the results of weatherability test, the compounds were confirmed to have higher light fastness grade and remaining fluorescence intensity than those of conventional commercial products.

Therefore, the fluorescent quinazolinone compound according to an exemplary embodiment of the present disclosure is colorless in daylight but may exhibit a high fluorescent intensity when irradiated with light in the near ultraviolet region. In addition, the fluorescent quinazolinone compound can be easily used with printed and plastic molded products since the compound not only has a high degree of light fastness and thermal stability but also high dispersibility. Further, the fluorescent quinazolinone compound according to an exemplary embodiment of the present disclosure can extend life cycle of the product by its high durability.

The abovementioned exemplary embodiments are intended to be illustrative, and not to limit the scope of the claims. Many alternatives, modifications, variations, and equivalents will be apparent to those skilled in the art. The features, structures, methods, and other characteristics of the exemplary embodiments described herein may be combined in various ways to obtain additional and/or alternative exemplary embodiments within an equivalent scope. Therefore, the technical scope of the rights for the present disclosure shall be decided by the appended claims and equivalents thereof.

The invention claimed is:

1. A near-ultraviolet stimulated light-emitting compound, represented by the following chemical formula III:

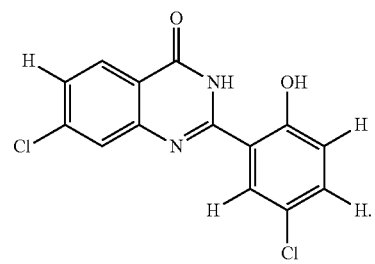

Chemical Formula III

2. A near-ultraviolet stimulated light-emitting compound, represented by the following chemical formula IV:

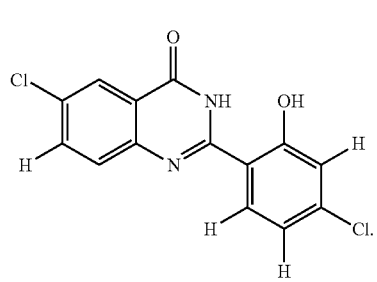

Chemical Formula IV

3. A near-ultraviolet stimulated light-emitting compound comprising:
   the near-ultraviolet stimulated light-emitting compound of claim 1; and
   a near-ultraviolet stimulated light-emitting compound comprising at least one binder selected from the group consisting of acrylic polymer, polyamide, polyurethane, polyester, polyethylene terephthalate, polycarbonate, and polypropylene.

4. A near-ultraviolet stimulated light-emitting compound comprising:
   the near-ultraviolet stimulated light-emitting compound of claim 2; and
   a near-ultraviolet stimulated light-emitting compound comprising at least one binder selected from the group consisting of acrylic polymer, polyamide, polyurethane, polyester, polyethylene terephthalate, polycarbonate, and polypropylene.

5. A method for producing the near-ultraviolet stimulated light-emitting compound of claim 1, the method comprising:
   condensation-reacting a 2-aminobenzamide, represented by the following chemical formula V; and a phenylaldehyde, represented by the following chemical formula VI:

Chemical Formula V

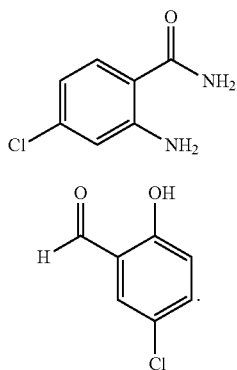

Chemical Formula VI

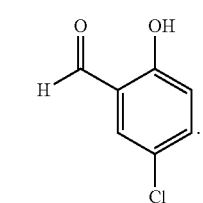

6. A method for producing the near-ultraviolet stimulated light-emitting compound of claim 2, the method comprising:
   condensation-reacting a 2-aminobenzamide, represented by the following chemical formula VII; and a phenylaldehyde, represented by the following chemical formula VIII:

Chemical Formula VII

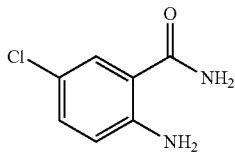

Chemical Formula VIII

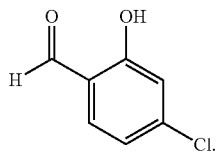

7. The method of claim 5, wherein the condensation reaction is accelerated by a catalyst.

8. The method claim 6, wherein the condensation reaction is accelerated by a catalyst.

9. The method of claim 7, wherein the catalyst is at least one selected from the group consisting of potassium permanganate, dichloro cyano benzoquinone, sodium bisulfite, scandium triflate, ammonium chloride, cupric chloride, stannic chloride, trifluoroacetic acid, tetrabutylammonium bromide, and p-toluenesulfonic acid.

10. The method of claim 8, wherein the catalyst is at least one selected from the group consisting of potassium permanganate, dichloro cyano benzoquinone, sodium bisulfite, scandium triflate, ammonium chloride, cupric chloride, stannic chloride, trifluoroacetic acid, tetrabutylammonium bromide, and p-toluenesulfonic acid.

11. The method of claim 5, wherein the condensation reaction is performed in at least one solvent selected from the group consisting of acetonitrile, ethyl alcohol, dimethylacetamide, and dimethylformamide.

12. The method of claim 6, wherein the condensation reaction is performed in at least one solvent selected from the group consisting of acetonitrile, ethyl alcohol, dimethylacetamide, and dimethylformamide.

13. A near-ultraviolet stimulated light-emitting ink comprising the near-ultraviolet stimulated light-emitting compound of claim 1.

14. A near-ultraviolet stimulated light-emitting ink comprising the near-ultraviolet stimulated light-emitting compound of claim 2.

* * * * *